United States Patent [19]
Walter

[11] Patent Number: 5,666,973
[45] Date of Patent: Sep. 16, 1997

[54] DEVICE TO REDUCE OR PREVENT NIGHT CLENCHING AND GRINDING OF TEETH AND SNORING

[76] Inventor: János Walter, 11, Kresz Géza utca, 1132 Budapest, Hungary

[21] Appl. No.: 493,593

[22] PCT Filed: Nov. 27, 1991

[86] PCT No.: PCT/HU91/00049
§ 371 Date: May 27, 1993
§ 102(e) Date: May 27, 1993

[87] PCT Pub. No.: WO92/09249
PCT Pub. Date: Jun. 11, 1992

Related U.S. Application Data

[63] Continuation of Ser. No. 66,088, May 27, 1993, abandoned.

[30] Foreign Application Priority Data

Nov. 28, 1990 [HU] Hungary .................. 7672/90

[51] Int. Cl.$^6$ .................................................. A61F 5/56
[52] U.S. Cl. ..................... 128/848; 128/861; 128/860
[58] Field of Search .................... 128/860, 861, 128/848, 859, 862, 207.14; 602/902

[56] References Cited

U.S. PATENT DOCUMENTS

| | | | |
|---|---|---|---|
| D. 32,565 | 4/1900 | Hooper | 128/859 |
| D. 300,059 | 2/1989 | Pier | D24/10 |
| 3,132,647 | 5/1964 | Corniello | 128/136 |
| 3,692,025 | 9/1972 | Greenberg | 128/861 |
| 3,871,370 | 3/1975 | McDonald | 128/860 |
| 4,304,227 | 12/1981 | Samelson | 128/860 |
| 4,676,240 | 6/1987 | Gardy | 128/848 |
| 4,997,182 | 3/1991 | Kussick | 128/861 |
| 5,042,506 | 8/1991 | Liberati | 128/848 |
| 5,092,346 | 3/1992 | Hays et al. | 128/861 |

FOREIGN PATENT DOCUMENTS

| | | | |
|---|---|---|---|
| 182387 | 5/1986 | European Pat. Off. | |
| 407949 | 1/1925 | Germany | |
| 3915501 | 11/1990 | Germany | 128/861 |
| 9205752 | 4/1992 | WIPO | 128/848 |

*Primary Examiner*—Sam Rimell
*Attorney, Agent, or Firm*—Young & Thompson

[57] ABSTRACT

A device is provided to prevent or reduce night clenching and grinding of teeth, as well as to impede snoring. The device is adapted to be placed into a mouth cavity of a patient and includes a conchiform element which is provided with an outer surface adapted to fit into the mouth cavity at an essentially closed position of upper and lower rows of the teeth. The conchiform element is also provided with an inner surface adapted to enclose a tip of a tongue of the patient entirely within the mouth cavity. An extension is adapted to be located under the tongue and has a notched indentation for receiving a ligament of the patient. A retaining element is fixed to the outer surface through a coupling member of a size sufficiently large enough to prevent sucking by the patient.

4 Claims, 3 Drawing Sheets

DEVICE TO REDUCE OR PREVENT NIGHT CLENCHING AND GRINDING OF TEETH AND SNORING

This application is a continuation of application Ser. No. 08/066,088, filed May 27, 1993, now abandoned.

BACKGROUND OF THE INVENTION

1. Field of the Invention

The invention relates to a device designed for the purpose of preventing or reducing night clenching and grinding of the teeth or snoring.

2. Description of the Related Art

Several methods have been experimented with to impede snoring and other unarticulated sounds unconsciously uttered during one's sleep. The essential feature of these methods is to provide an unobstructed air passage between the tongue (root of the tongue) and the palate (especially the soft part of it) by means of a mechanism preventing the tongue and palate from getting shut up against each other. Devices of such kind have been described in the patent specifications EP A 0182387, DE 407949 and U.S. Pat. No. 3132647. From these methods the one mentioned first causes the least discomfort to the patient, but it is rather complicated. According to this method an acrylate resin bar is attached to both sides of the upper rear molars through an acrylate resin spacer in the rear region of the hard palate. This arrangement is, to some extent, capable of preventing snoring, but its use is inconvenient, and it is rather complicated and costly to prepare. Furthermore, it is unsuitable for reducing or preventing the night grinding and excessive clenching of the teeth.

SUMMARY OF THE INVENTION

The aim to be achieved is, by eliminating the above deficiencies, to provide for a method simpler, easier to get accustomed to and more convenient in its use than those of earlier designs, the device being capable, at the same time or additionally, of preventing snoring, reducing or impeding night grinding or excessive clenching of the teeth.

The device developed for achieving the above aim is a shell-like or conchiform element convex at its outside and concave at its inner side, with its inner surface matching to the shape of the tip of the tongue and with its outer surface to the shape of the lower and upper rows of teeth and to that of the palate.

No clamping element is applied for fixing the above means either to the tongue or to the rows of teeth or to the palate, the invention being based on the recognition that no fixing is required after a short period of getting accustomed to said properly shaped element placed into the mouth, said means being kept in place, even in the unconscious state of sleeping, owing to the excellent innervating capability of the tongue. Even in the case of a slight displacement of said element, the conditional reflex becomes active to bring about the adjustments required for restoring proper position of the element. The corrective intervention of this reflex becomes increasingly effective after a not too long period of using the element.

By the same recognition, such a conchiform means is equally suitable for impeding or preventing the grinding and clenching of the teeth.

The element serving for the prevention of snoring is provided with an anti-tilting extension, preventing the element complying with the present invention from excessive tilting even with the mouth widely opened.

The outer arch of the element serving for impeding the grinding of the teeth is tightly fitted to the inside of the row of teeth in the direction perpendicular to that or the bit, preventing thereby lateral relative displacement between upper and lower rows of the teeth (in the direction of grinding).

The element impeding the clenching of the teeth is designed to fit the cavity of the mouth being in a slightly opened state, i.e. with an arch in the plane of the direction of the bite, tightly fitting to the shape of the rows of teeth and palate in slightly opened position of the mouth. Owing to this shape of the element upon clenching of the teeth, an uncomfortable feeling of pressure arises in the mouth instinctively relieved by slight opening of the mouth, even while asleep.

BRIEF DESCRIPTION OF THE DRAWINGS

The invention and its further features and advantages will be described with reference to the embodiments shown as examples in the attached drawings. In the drawing.

DETAILED DESCRIPTION OF THE PREFERRED EMBODIMENTS

Figure 1:
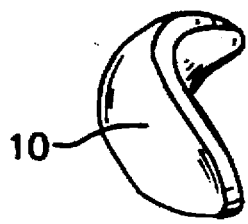
FIG. 1 is an embodiment of the invention to impede clenching of the teeth.
Figure 2:
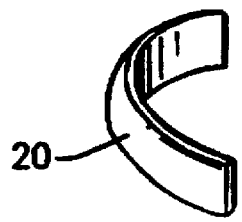
FIG. 2 is an embodiment of the invention serving for preventing the grinding of the teeth.
Figure 1A:
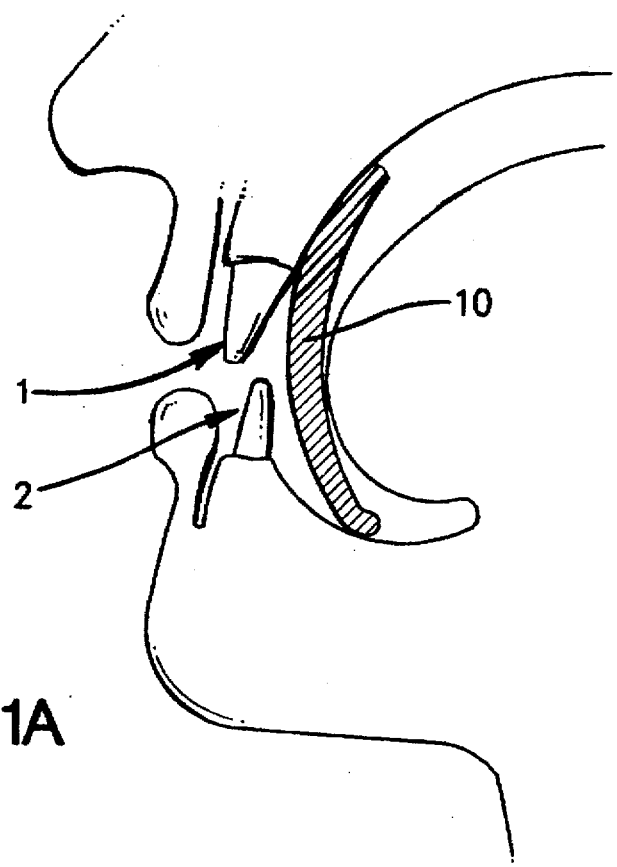
FIG. 1a is a cross-sectional side view of the embodiment in FIG. 1.
Figure 2A:
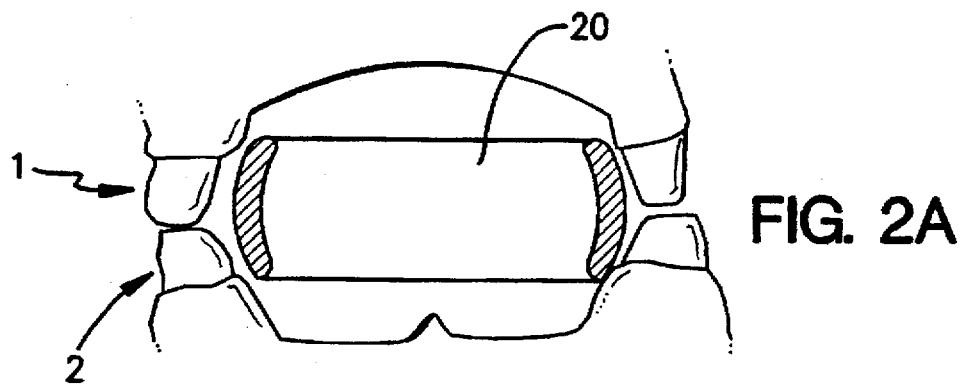
FIG. 2a is a cross-sectional rear view of the embodiment in FIG. 2.

FIG. 1 shows a device 10 impeding the clenching of the teeth, enclosing ⅓–¼ part of the user's tongue at its frontal end or tip. The device 10 fits closely to the user's upper and lower rows of teeth 1, 2 shown in FIG. 1a and, more specifically, in the inner frontal part of the rows of teeth 1, 2 in the mouth cavity when in a slightly opened position. It is easy to see that the rows of teeth 1 and 2 could only be clenched unhindered after withdrawing backwards the device 10 and the tongue 3 to a considerable extent. In that case, however, on the one hand, the device 10 would come into contact with parts of the mouth cavity causing an uncomfortable feeling and, on the other hand, a withdrawal of the tongue 3 to such an extent would also cause inconvenience to the user; therefore, the patient does not entirely close his rows of teeth 1 and 2 even when asleep, so the required effect can be achieved. The device shown in FIG. 1 can be used also for preventing the grinding of the teeth, but for this purpose a smaller device 20 shown in FIG. 2 is just as well suitable. This device 20 fits in a lateral direction to the inside of the rows of teeth 1 and 2 as seen in FIG. 2a, with the jaws kept clamped or slightly opened corresponding to an increased height of bite (i.e. the upper and lower teeth are slightly displaced from their closed position in a vertical direction).

Lateral displacement of the rows of teeth 1 and 2 from a biting position and thus the grinding of the teeth is prevented by the lateral fit. During sleep, the device 20 is maintained in the desired position by the user's tongue.

Figure 3:
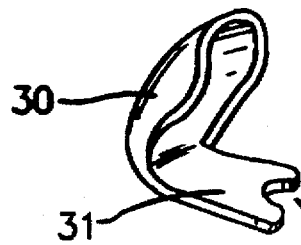
FIG. 3 is an embodiment of the invention to impede snoring.
Figure 5:
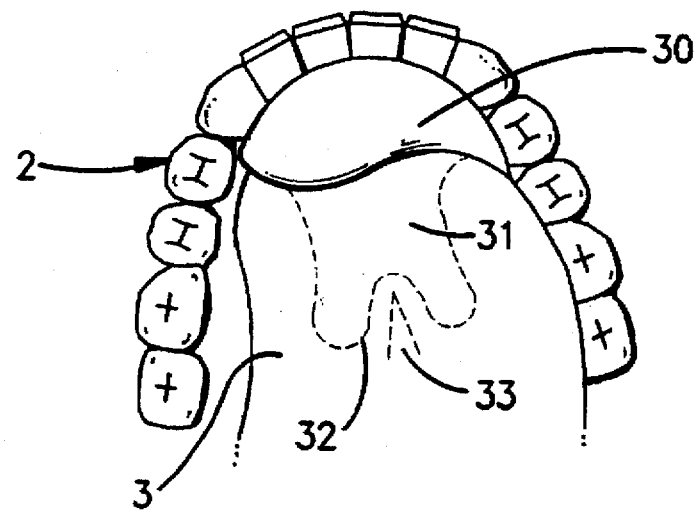
FIG. 5 shows relative position of the device complying with the invention and that of the tongue and rows of teeth during use, in the plane perpendicular to the direction of the bite.
Figure 6:
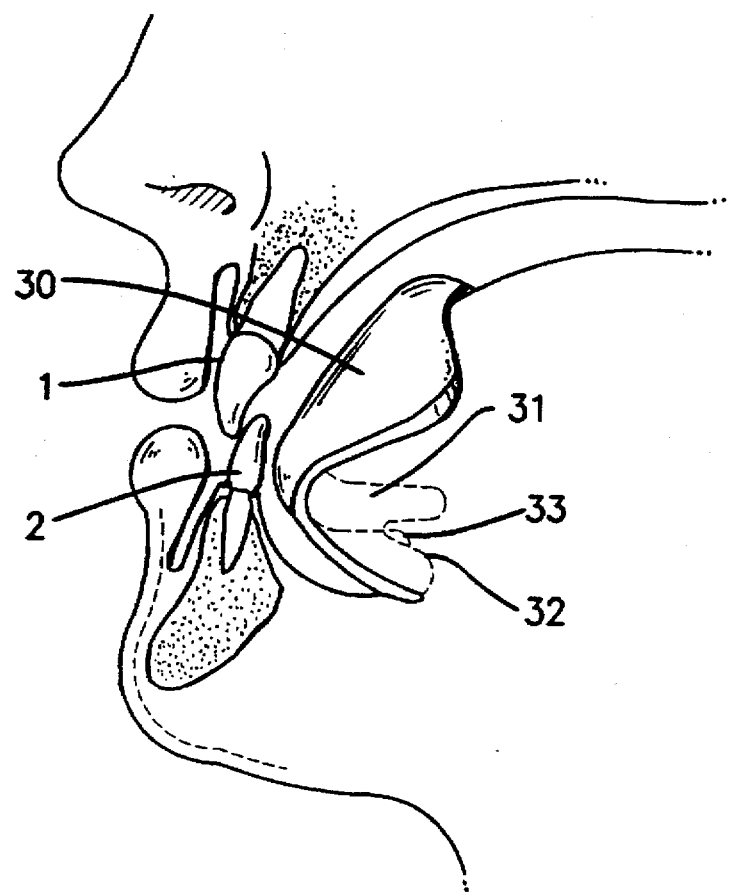
FIG. 6 is an embodiment of the device complying with the invention serving for the prevention of snoring.

An anti-snoring device 30 is shown in FIGS. 3, 5 and 6. The inner surface of the device fits to the frontal ⅓–¼ part of the patient's tongue 3, its outer surface to the closed rows 1 and 2 of the teeth and to the part of the mouth cavity adjacent to said rows. The device 30 is provided with an anti-tilting extension 31, with an indentation 32 notched at its middle part to receive the ligament of the tongue. The tongue 3 of the patient is enclosed almost equally from below and from above by the device 30, i.e. one half of the latter is located over the tongue 3 and the other half under it.

FIGS. 5 and 6 show the device 30 of the invention inserted in the user's mouth. Especially from FIG. 6, it can clearly be seen that the shape of the device 30 fits well into the mouth cavity, and its displacement from the desired position is effectively prevented by the anti-tilting extension 31.

The devices 10, 20, 30 of the invention are made of an innocuous elastic or rigid material, e.g. some kind of plastic used in dentistry, preferably acryl resin. Wall thicknesses are between approx. 2 and 3 mm, depending on the strength of the material used and on the physiological endowments of the patient. An impression can be taking from the respective parts of the mouth cavity to enable individual forming of the device, because taking this impression is the safest way to obtain the desired result and, at the same time, accommodation problems can also be minimized.

The use of the devices 10, 20, 30 complying with the invention can easily be accustomed to, since they do not modify the position of the patient's tongue. Before starting with the night use of the device, it is expedient to wear it in a waking state for the sake of accommodation through a period of a few days, preferably in the evenings before going to bed. In the accommodation period the wearing time can be increased gradually, while the foreign body in the mouth becomes more and more tolerated. The night use can be attempted after a few days and on wakening from the first sleep (even half asleep) the device may be taken out.

Figure 4:
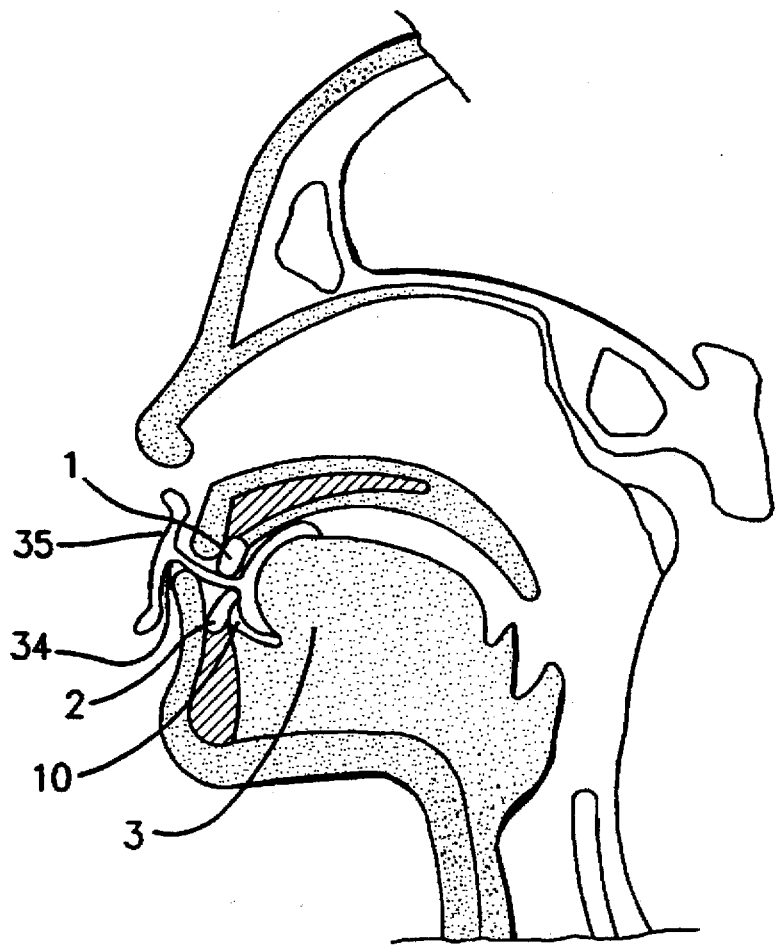
FIG. 4 is the embodiment of the invention provided with a retaining member shown inserted in the mouth with the rows of teeth in slightly opened position.
Figure 4A:
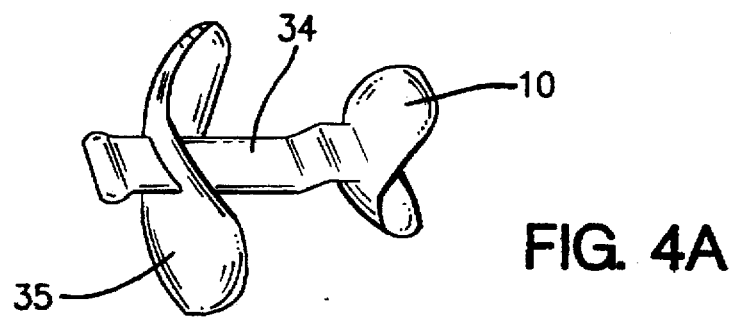
FIG. 4a is a perspective view of the embodiment in FIG. 4.

In spite of getting accustomed to it easily and to its safety, some patients feel fear of using the device complying with the invention. To avoid this psychic inhibition and in order to increase safety by means of an elastic or rigid coupling member 34 shown in FIGS. 4 and 4a or by e.g. dental floss, a large-sized lightweight retaining element 35, not obstructing the breathing, can be attached to the device 10 so that it may be discarded after the ceasing of psychic inhibition. This becomes soon possible due to the excellent innervation of the tongue, rendering it capable, even when the patient is asleep, of keeping the device in the desired position, while the slightest displacement will give rise to an immediate corrective reaction. The coupling member 34 may though increase the height of the bite (generally this is the case with all embodiments), but this increase is not disturbing.

According to the evidence of several hundred cases, the device complying with the invention, if properly used, can safely be applied and can become easily accustomed to, without disturbing the sleep of the user.

Not a single case of swallowing or inhaling (sucking into the trachea) has occurred. Obviously, the device complying with the invention cannot be used if the mouth cannot be kept closed, i.e. in all cases when breathing through the nose is hampered with coughing, sneezing, nasal discharge, a febrile condition, facial paralysis, states following an attack of apoplexy, epilepsy, asthma, and Sjörgren syndrome (chronic dryness of the mouth), but its use should be avoided under alcoholic influence, while being under the effect of sedatives or narcotics, by patients having cerebral sclerosis or being otherwise mentally retarded and, generally, in all cases when a risk would be involved with its use. The risk can, of course, be reduced or excluded by means of the retaining element 35, making the device 10, 20, 30 of the invention act like a baby pacifier.

Experience has also shown that the device complying with the invention prevents the tongue from sliding back as a shapeless mass obstructing passage of the air. That is why the condition close to suffocation does not develop—otherwise characteristic of snoring that may several times, night by night —overburdening the heart and blood circulation. The patient's sleep becomes restful and they awake more nimbly than before. After prolonged use, conditional reflexes acting also while asleep develop, and in certain cases the device can be applied less frequently, or it may be fully omitted. In some cases the size of the device can be reduced after one or two months, and it has to be kept in the mouth every other night only.

If the device is removed on awakening from the first sleep while still being half asleep, the spastic compression or grinding of the teeth does not reoccur—at least in the majority of cases. This observation does not apply to snoring, since in the case of such complaint, the device 30 complying with the invention has, generally, to be kept inserted during the entire period of the sleep.

Of course, the success of using the devices 10, 20, 30 is also dependent on the posture assumed during sleeping. The most favorable position is to lie on the side, whereas lying on one's back, the snoring, and in the case of lying prone, the clenching and grinding of the teeth are those most probably occurring, due to the stretched state of the masticatory muscle.

Experience has shown that in some cases the application of the devices 10, 20, 30 can be omitted once and for all, after some period of time. The time of omission cannot be determined in advance, because this will depend, among other factors, on the patient's age, severity of complaints and on how long the complaints subsisted. Omission should be attempted gradually, or the size of the device can be reduced. However, especially, in the case of snoring, frequent relapse can occur. In such cases the conditional reflexes can quickly be reactivated by repeated use of the device through a period of a few successive nights.

What is claimed is:

1. A device to prevent or reduce night clenching and grinding of teeth, as well as to impede snoring, said device being adapted to be held in the mouth of the user, the device comprising a conchiform element (10) having a concave side and a convex side, a strip (34) secured to said convex side, and a concave member (35) having a concave side and a convex side, said concave member (35) being carried by said strip (34) in spaced relation to said conchiform element, said concave side of said concave member (35) facing in a same direction as said concave side of said conchiform element (10), said conchiform element (10) being elongated in a first direction and said concave member (35) being elongated in a second direction, said first and second directions being transverse to each other.

2. A device as claimed in claim 1, said strip being elastic.

3. A device as claimed in claim 1, said conchiform element (10) being elastic.

4. A device as claimed in claim 1, said strip being flattened in said second direction.

* * * * *